United States Patent
Bronstein et al.

(10) Patent No.: US 11,375,939 B2
(45) Date of Patent: Jul. 5, 2022

(54) BIOSIGNAL ACQUISITION METHOD AND ALGORITHMS FOR WEARABLE DEVICES

(71) Applicant: RAMOT AT TEL AVIV UNIVERSITY LTD., Tel Aviv (IL)

(72) Inventors: Alex Bronstein, Haifa (IL); Evgeny Tsizin-Goldman, Ramat Gan (IL)

(73) Assignee: RAMOT AT TEL AVIV UNIVERSITY LTD., Tel Aviv (IL)

(*) Notice: Subject to any disclaimer, the term of this patent is extended or adjusted under 35 U.S.C. 154(b) by 553 days.

(21) Appl. No.: 16/316,627

(22) PCT Filed: Jul. 12, 2017

(86) PCT No.: PCT/IB2017/054196
§ 371 (c)(1),
(2) Date: Jan. 10, 2019

(87) PCT Pub. No.: WO2018/011720
PCT Pub. Date: Jan. 18, 2018

(65) Prior Publication Data
US 2019/0290152 A1    Sep. 26, 2019

Related U.S. Application Data

(60) Provisional application No. 62/361,529, filed on Jul. 13, 2016.

(51) Int. Cl.
*A61B 5/30* (2021.01)
*A61B 5/00* (2006.01)
(Continued)

(52) U.S. Cl.
CPC ............. *A61B 5/30* (2021.01); *A61B 5/0042* (2013.01); *A61B 5/0531* (2013.01);
(Continued)

(58) Field of Classification Search
CPC ......... A61B 5/296; A61B 5/389; A61B 5/681; A61B 5/0531; A61B 2562/0214; A61N 1/0484; G06F 3/017
See application file for complete search history.

(56) References Cited

U.S. PATENT DOCUMENTS 4,495,950 A * 1/1985 Schneider ............ A61B 5/6831
600/521
5,905,489 A * 5/1999 Takahama ............. G06F 3/0412
345/174
(Continued)

FOREIGN PATENT DOCUMENTS

CN     203815454 U    9/2014
CN     104302351 A    1/2015
(Continued)

OTHER PUBLICATIONS

Tommaso., "Parallel Modeling of the Electric Field Distribution in the Brain", Doctor Thesis, Alma Mater Studiorum—University of Bologna, Cycle XXIII—ING-INF/01, pp. 1-135, year 2011.
(Continued)

*Primary Examiner* — Sean P Dougherty
(74) *Attorney, Agent, or Firm* — Kligler & Associates Patent Attorneys Ltd (57) ABSTRACT

Apparatus, including a set of N electrodes (22), configured to be located in proximity to an epidermis (24) of a subject, and to acquire signals generated by electric sources within the subject. The apparatus also includes a set of M channels, configured to transfer the signals, where M is less than N, and a switch (40), configured to select, repetitively and randomly, M signals from the N electrodes and to direct the M signals to the M channels. The apparatus further includes a processor (28), configured to activate the switch, and to receive and analyze the M signals from the M channels so
(Continued)

as to determine respective positions of the electric sources within the subject.

23 Claims, 9 Drawing Sheets

(51) Int. Cl.
| | |
|---|---|
| A61N 1/36 | (2006.01) |
| A61B 5/0531 | (2021.01) |
| A61N 1/04 | (2006.01) |
| A61B 5/1495 | (2006.01) |
| A61N 1/08 | (2006.01) |
| G06F 3/01 | (2006.01) |
| A61N 1/378 | (2006.01) |
| A61B 5/291 | (2021.01) |
| A61B 5/296 | (2021.01) |
| A61B 5/316 | (2021.01) |
| A61B 5/369 | (2021.01) |
| A61B 5/389 | (2021.01) |
| A61B 5/24 | (2021.01) |

(52) U.S. Cl.
CPC .......... *A61B 5/1495* (2013.01); *A61B 5/2415* (2021.01); *A61B 5/291* (2021.01); *A61B 5/296* (2021.01); *A61B 5/316* (2021.01); *A61B 5/369* (2021.01); *A61B 5/389* (2021.01); *A61B 5/681* (2013.01); *A61B 5/6803* (2013.01); *A61B 5/6822* (2013.01); *A61B 5/6823* (2013.01); *A61B 5/6824* (2013.01); *A61B 5/6828* (2013.01); *A61B 5/6829* (2013.01); *A61B 5/6831* (2013.01); *A61B 5/7207* (2013.01); *A61N 1/0484* (2013.01); *A61N 1/08* (2013.01); *A61N 1/36* (2013.01); *A61N 1/378* (2013.01); *G06F 3/015* (2013.01); *A61B 2560/0209* (2013.01); *A61B 2562/0214* (2013.01); *G06F 3/011* (2013.01); *G06F 3/017* (2013.01)

(56) References Cited

U.S. PATENT DOCUMENTS

| | | | | |
|---|---|---|---|---|
| 7,130,694 | B1* | 10/2006 | Voelkel | A61N 1/36038 607/55 |
| 7,697,979 | B2 | 4/2010 | Martinerie et al. | |
| 7,809,434 | B2 | 10/2010 | Kofol et al. | |
| 8,032,209 | B2 | 10/2011 | He et al. | |
| 9,415,214 | B2* | 8/2016 | Moore | A61N 1/36034 |
| 10,228,242 | B2* | 3/2019 | Abovitz | A63F 13/00 |
| 2003/0069514 | A1* | 4/2003 | Brody | A61B 5/296 600/546 |
| 2004/0006279 | A1 | 1/2004 | Arad (Abboud) | |
| 2006/0041203 | A1* | 2/2006 | Wolf | A61B 5/316 600/544 |
| 2006/0085049 | A1 | 4/2006 | Cory et al. | |
| 2006/0165811 | A1* | 7/2006 | Black | A61B 5/4041 424/570 |
| 2008/0082012 | A1* | 4/2008 | Gunderson | A61N 1/37 600/509 |
| 2008/0132800 | A1* | 6/2008 | Hettrick | A61B 5/1107 600/509 |
| 2008/0161714 | A1 | 7/2008 | Ahonen et al. | |
| 2008/0208284 | A1* | 8/2008 | Rezai | A61N 1/36071 607/45 |
| 2008/0312523 | A1* | 12/2008 | Dunseath | A61B 5/369 600/383 |
| 2009/0033333 | A1 | 2/2009 | Gribova et al. | |
| 2009/0054800 | A1 | 2/2009 | Martinerie et al. | |
| 2009/0082691 | A1* | 3/2009 | Denison | A61B 5/374 600/544 |
| 2011/0257506 | A1 | 10/2011 | Baillet et al. | |
| 2011/0319777 | A1 | 12/2011 | Mehrotra et al. | |
| 2012/0101545 | A1* | 4/2012 | Wahlstrand | A61N 1/37288 607/60 |
| 2012/0157868 | A1* | 6/2012 | Pekonen | A61B 5/0245 600/509 |
| 2012/0232376 | A1 | 9/2012 | Crevecoeur et al. | |
| 2012/0265261 | A1* | 10/2012 | Bikson | A61N 1/0476 607/2 |
| 2012/0310105 | A1* | 12/2012 | Feingold | A61B 5/374 600/544 |
| 2013/0041235 | A1 | 2/2013 | Rogers et al. | |
| 2013/0150697 | A1* | 6/2013 | Imai | A61B 5/296 600/384 |
| 2013/0321009 | A1* | 12/2013 | Aliakseyeu | G06F 3/015 324/699 |
| 2014/0031952 | A1* | 1/2014 | Harshbarger | A61B 5/7264 623/25 |
| 2014/0058528 | A1* | 2/2014 | Contreras-Vidal | A61B 5/291 623/25 |
| 2014/0198035 | A1* | 7/2014 | Bailey | G02B 27/017 345/156 |
| 2014/0257129 | A1 | 9/2014 | Choi et al. | |
| 2014/0296941 | A1 | 10/2014 | King et al. | |
| 2015/0011857 | A1* | 1/2015 | Henson | A61B 5/6831 600/383 |
| 2015/0072326 | A1* | 3/2015 | Mauri | A61B 5/0531 434/247 |
| 2015/0148641 | A1* | 5/2015 | Morun | H05K 1/162 600/372 |
| 2015/0185853 | A1* | 7/2015 | Clausen | G16H 40/63 600/546 |
| 2015/0245928 | A1* | 9/2015 | Kao | G05B 15/02 700/90 |
| 2015/0272483 | A1* | 10/2015 | Etemad | A61B 5/05 600/409 |
| 2015/0272501 | A1 | 10/2015 | Maceachern et al. | |
| 2015/0282768 | A1* | 10/2015 | Luna | A61B 5/02444 600/301 |
| 2015/0297145 | A1* | 10/2015 | Luna | A61B 5/4866 600/301 |
| 2015/0359491 | A1* | 12/2015 | Luna | A61B 5/0205 600/301 |
| 2016/0100803 | A1* | 4/2016 | Korzinov | G06N 5/022 600/301 |
| 2016/0354604 | A1* | 12/2016 | Kent | A61N 1/36034 |
| 2017/0123528 | A1* | 5/2017 | Hu | G06F 3/0412 |
| 2017/0238812 | A1* | 8/2017 | Atlas | A61B 5/0205 |
| 2018/0028810 | A1* | 2/2018 | Schwarz | A61N 1/36031 |
| 2018/0036531 | A1* | 2/2018 | Schwarz | A61N 1/0484 |
| 2018/0279939 | A1* | 10/2018 | Madsen | A61B 5/4094 |
| 2020/0282223 | A1* | 9/2020 | Schwemmer | B25J 13/06 |

FOREIGN PATENT DOCUMENTS

| | | |
|---|---|---|
| CN | 105266807 A | 1/2016 |
| WO | 2010129026 A1 | 11/2010 |
| WO | 2014051590 A1 | 4/2014 |
| WO | 2014208074 A1 | 12/2014 |
| WO | 2015100482 A1 | 7/2015 |

OTHER PUBLICATIONS

Frank., "An Accurate, Clinically Practical System For Spatial Vectorcardiography", Circulation, vol. XIII, May, pp. 737-749, year 1956.

Nenonen et al., "Total information extracted from MEG measurements", International Congress Series 1300, pp. 245-248, year 2007.

International Application # PCT/IB2017/054196 search report dated Oct. 23, 2017.

Medvedovsky et al., U.S. Appl. No. 16/290,988, filed Mar. 4, 2019.

Hamalainen et al., "Magnetoencephalography—Theory, Instrumentation and Applications to the Noninvasive Study of Human Brain Function", Reviews of Modern Physics, vol. 65, No. 2, pp. 413-497 + 8 sheets of figures, Apr. 1993.

(56) References Cited

OTHER PUBLICATIONS

Wolters et al., "A Parallel Algebraic Multigrid Solver for Finite Element Method Based Source Localization in the Human Brain", Computing and Visualization in Science, pp. 165-177, year 2002.
IN Application # 201947003483 Office Action dated May 26, 2021.
European Application # 17827093.0 search report dated Jan. 23, 2020.
Holder et al.,"Part 1 of Electrical Impedance Tomography: Methods, History and Applications", Institute of Physics Publishing, pp. 1-61, Dec. 21, 2004.
Kemppainen et al., "Channel capacity of multichannel magnetometers," Advances in Biomagnetism, Plenum Press, pp. 635-638, year 1989.
Elazar et al., "Impedance Changes during Epileptic Seizures", Epilepsia Journal, Elsevier Publishing Company, vol. 7, issue 4, pp. 291-307, year 1966.
Nenonen et al., "Total information of multichannel MEG sensor arrays," Proceedings of the 14th International Conference on Biomagnetism, Boston, USA, pp. 630-631, Aug. 8-12, 2004.
Cuffin et al., "Tests of EEG Locahzation Accuracy Using Implanted Sources in the Human Brain", Annals of Neurology, vol. 29, issue 2, pp. 132-138, Feb. 1991.
CN Application #201780043260.9 Office Action dated Jan. 24, 2022.

\* cited by examiner

BIOSIGNAL ACQUISITION METHOD AND ALGORITHMS FOR WEARABLE DEVICES

CROSS-REFERENCE TO RELATED APPLICATION

This application claims the benefit of U.S. Provisional Patent Application 62/361,529, filed Jul. 13, 2016, which is incorporated herein by reference.

FIELD OF THE INVENTION

This invention relates generally to signal acquisition, and specifically to biological signal acquisition.

The work leading to this invention has received funding from the European Research Council under the European Union's Seventh Framework Programme (FP7/2007-2013)/ERC grant agreement no. 335491.

BACKGROUND OF THE INVENTION

According to a 2014 study by Forbes, 71% of 16-to-24 year olds want wearable technology. Although at its beginning, the trend for using this technology is growing rapidly, allowing the users of wearable devices such as SmartWatch, Smart wristband, SmartCloth or Virtual Reality headsets to control electronic devices or monitor their physical parameters for entertainment or health care. However, one of the main drawbacks of present devices is their low signal quality and poor reliability due, for example, to the motion of the devices while in use. Furthermore, the number of sensing channels of the devices is limited by the cost, and reduced numbers of channels influences the signal quality.

SUMMARY OF THE INVENTION

An embodiment of the present invention provides apparatus, including:

a set of N electrodes, configured to be located in proximity to an epidermis of a subject, and to acquire signals generated by electric sources within the subject;

a set of M channels, configured to transfer the signals, where M is less than N;

a switch, configured to select, repetitively and randomly, M signals from the N electrodes and to direct the M signals to the M channels; and a processor, configured to activate the switch, and to receive and analyze the M signals from the M channels so as to determine respective positions of the electric sources within the subject.

In a disclosed embodiment the processor is configured to determine respective amplitudes of the electric sources.

In a further disclosed embodiment the apparatus includes respective current sources, and the processor is configured to activate the switch so as to inject respective predetermined currents from the sources between selected pairs of the N electrodes. Typically, the injected currents have a plurality of baseband frequencies. The injected currents may have frequencies between 10 Hz and 100 GHz.

In a yet further disclosed embodiment the switch includes a matrix of switches.

In an alternative embodiment at least one of the electrodes is capacitively coupled to the epidermis.

In a further alternative embodiment the processor is configured to short-circuit together selected ones of the N electrodes.

In a yet further alternative embodiment the signals include sparse activations.

There is further provided, according to an embodiment of the present invention a method, including:

locating a set of N electrodes in proximity to an epidermis of a subject so as to acquire signals generated by electric sources within the subject;

transferring the signals via a set of M channels, where M is less than N;

selecting repetitively and randomly, M signals from the N electrodes, and directing the M signals to the M channels via a switch: and activating the switch, and receiving and analyzing the M signals from the M channels so as to determine respective positions of the electric sources within the subject.

There is further provided, according to an embodiment of the present invention, a method, including:

positioning a set of N electrodes on an epidermis of a subject, wherein the electrodes are configured to acquire signals from the subject;

selecting a subset of the N electrodes that are in proximity with each other;

measuring impedances of the subset relative to each other; and when the impedances change, using the change of impedances to estimate a change in the acquired signals, and applying the change in the acquired signals so as to correct the acquired signals.

In a disclosed embodiment, measuring the impedances includes injecting a predetermined signal into one of the subset, and measuring potentials of the acquired signals, generated in response to the injection, at remaining electrodes of the subset.

In a further disclosed embodiment a motion of the subject causes the change in the acquired signals.

In a yet further disclosed embodiment the signals originate from within the subject.

There is further provided, according to an embodiment of the present invention, a method, including:

positioning a set of N electrodes on an epidermis of a subject, wherein the electrodes are configured to acquire signals from the subject;

while the subject is performing an initial gesture, injecting a signal into the subject via at least one of the N electrodes, and measuring N respective potentials generated at the N electrodes in response to the injection;

formulating an initial matrix of the N respective potentials and the at least one of the N electrodes;

forming a correspondence between the initial matrix and the initial gesture; and using the correspondence to recognize that a subsequent gesture of the subject corresponds to the initial gesture.

The method may also include injecting the signal into the subject via each of the N electrodes, and formulating the initial matrix as an N×N matrix of the N respective potentials and the N electrodes.

In a disclosed embodiment using the correspondence to recognize that the subsequent gesture of the subject corresponds to the initial gesture includes injecting the signal into the subject via the at least one of the N electrodes while the subsequent gesture is being performed, measuring further N respective potentials generated at the N electrodes in response to the injection, formulating a subsequent matrix of the further N respective potentials and the at least one of the N electrodes, and comparing the subsequent matrix with the initial matrix.

There is further provided, according to an embodiment of the present invention, apparatus, including:

a set of N electrodes configured to be positioned on an epidermis of a subject, wherein the electrodes are configured to acquire signals from the subject;

a switch connected to the set of N electrodes; and a controller configured to:

operate the switch so as to select a subset of the N electrodes that are in proximity with each other, measure impedances of the subset relative to each other, and when the impedances change, use the change of impedances to estimate a change in the acquired signals, and apply the change in the acquired signals so as to correct the acquired signals.

Typically, measuring the impedances includes injecting a predetermined signal into one of the subset via the switch, and measuring potentials of the acquired signals, generated in response to the injection, via the switch at remaining electrodes of the subset.

There is further provided, according to an embodiment of the present invention apparatus, including:

a set of N electrodes configured to be positioned on an epidermis of a subject, wherein the electrodes are configured to acquire signals from the subject;

a switch connected to the set of N electrodes; and a controller configured to:

while the subject is performing an initial gesture, inject a signal into the subject via at least one of the N electrodes, and measure N respective potentials generated at the N electrodes in response to the injection;

formulate an initial matrix of the N respective potentials and the at least one of the N electrodes;

form a correspondence between the initial matrix and the initial gesture; and use the correspondence to recognize that a subsequent gesture of the subject corresponds to the initial gesture.

The present invention will be more fully understood from the following detailed description of the embodiments thereof, taken together with the drawings in which:

DETAILED DESCRIPTION OF EMBODIMENTS

Overview

Recently there has been introduced a novel family of methods for signal acquisition and processing called compressive sensing. Compressive sensing is based on the observation that many signals in nature are "sparse" in some "basis." The basis is herein called a dictionary, and it may be thought as a set of prototype signals. The signals in nature, referred to above, can be represented using a small number of the prototype signals, also termed elements or atoms, of this basis. Accordingly, sampling these signals using the Nyquist rate introduces redundancy. This observation permits developing mathematical theories for making use of this redundancy in both acquisition and processing of these signals to reduce the sampling frequency, memory requirements, and the power consumption of the acquisition and processing systems.

For realistic signals obeying some natural statistical properties, machine learning algorithms can be developed for both learning an optimal dictionary and learning signal decoding algorithms. Using this dictionary for the compressively sampled signals reduces the computational burden of signal restoration algorithms to levels suitable for the real time applications.

There is evidence showing that electrophysiological signals have a sparse nature. For instance, usually only a small fraction of our brain is active during a specific task. Consequently, embodiments of the present invention use mathematical ideas based on the modeling of the electromagnetic properties of biological signal propagation within biological tissues to provide a new method for biosignals acquisition, together with algorithms for their processing. In this method a controllable set of switches between the electrodes interfacing with the subject is altered in time during the electrophysiological signal acquisition and these combinations of signals lead into acquisition channels.

Not being restricted by the number of acquisition channels (which in our system is determined by the number of active sources rather than by the number of sensing elements as in a conventional design) using our method it is possible to place many sensing elements on a wristband for an electromyogram (EMG) or on a cap/helmet for an electroencephalogram (EEG) and still achieve an improved signal quality using a small number of A/D channels. We can achieve this by short-circuiting different numbers of sensing elements near the same sensing place, and in so doing we change the capacitive coupling between an equivalent electrode and the body. In addition, since the capacitive coupling depends on the distance of the electrodes from the body, our method enables encoding the mutual position of the sensor electrodes and the body, thus reducing any motion artifact.

(In general, we may place the sensing elements referred to above on any portion of the epidermis of a living creature.)

Moreover, there is ongoing research for gesture identification based on wrist shape identification. Accordingly, not only does the ability to track the relative position of the sensor electrodes and the body surface passively compensate for any motion artifact of the electrophysiological signal acquisition, but it also has a value in itself for a gesture recognition system.

Embodiments of the present invention use algorithms from the compressed sensing and machine learning families to extract new information that is not contained in prior art systems, while maintaining a low number of acquisition channels. Processing of this information increases the robustness of wearable devices to movement artifacts on the one hand, and reduces the number of the required measuring channels on the other hand. We thus increase the quality/cost ratio of the wearables, and also reduce the power consumption of wireless wearable devices leading to longer battery life. It will be understood that embodiments of the present invention may be advantageously used for medical devices, for instance by reducing the costs of present dense EEG systems (comprising many electrodes) and make embodiments using our invention affordable for any clinic.

In embodiments of the present invention that are configured for identifying gestures, a dictionary for different gestures is learned by following the temporal patterns of involved electric sources (e.g., muscles and the wrist contour shapes for EMG) and adapting the temporal patterns of switching circuitry. After proper modeling of the signal propagation within the biological tissues, and taking motion artifacts into account, the switches corresponding to the sensors most sensitive to the muscles involved in a relevant gesture will be more frequent in the temporal pattern of the switching circuitry.

The above description has assumed a passive acquisition of signals. However, the passive technique can be enriched by the active technique of electrical capacitance tomography (or in general electrical impedance tomography). In this technique currents are injected through electrodes around the body and measured voltages at other electrodes are used to estimate the internal impedance distribution. The active technique also improves the modelling of the electrophysiological signal propagation and enables discrimination between different geometries, i.e., gestures, of the body under test while recording electrophysiological signals.

DETAILED DESCRIPTION

Theory
EEG Inverse Problems

The electromagnetic activity of the brain is modeled by current dipoles within inhomogeneous conducting media. According to this modeling the gain matrix G of the EEG forward problem is calculated. The columns of G comprise the electrostatic potentials sampled at the sensors' positions over the scalp induced by unit dipoles assumed to be placed in different locations and orientated perpendicularly to the human cortex. The inverse EEG problem aims to find the timecourses X of the current dipoles given the matrix of the measurements M=GX+E, where E represents the additive noise, and X is the variation of current dipoles amplitudes with time. Various regularization terms f(X) typically should be added to obtain meaningful solutions:

$$X^* = \operatorname*{argmin}_{X}\left(\frac{1}{2}\|M - GX\|_2^2 + \lambda f(X)\right)$$

where $\lambda$ is a regularization parameter.

The weighted minimum energy (wMNE) solution is obtained by imposing a weighted $l_2$ norm regularization $$f(X)_{l_2} = \sqrt{\sum_{s=1}^{P} w_s x_s^2}, \ w_s > 0$$

where X is a vector, having elements $x_S$ multiplied by weights $w_S$.

This regularization typically leads to smeared solutions. It is more physiologically plausible to assume sparse activations of the brain cortex (i.e., a small fraction of the brain is activated at any given time) for realistic tasks.

Real Time $l_1$ Norm Minimization Algorithm

Ideally, the sparsity inducing norm is $l_0$ norm (minimizing the number of acting electric sources). However, the optimization problem of minimizing the $l_0$ norm regularization leads to a high computational burden that increases exponentially with the number of terms. As is well known, the $l_1$ norm regularization term $$f(X) = \sqrt{\sum_{s=1}^{P} w_s |x|_s}, \ w_s > 0$$

is also a sparsity inducing regularization term (being "sufficiently close" to the $l_0$ norm). To solve the optimization problem corresponding to the $l_1$ norm the following iterations have to be performed:

$$X^0 = 0$$
$$B^{k+1} = WM + SX^k$$
$$X^{k+1} = \pi_{\frac{\lambda}{\alpha}}(B^{k+1})$$

Where $$\alpha = \lambda_{max}(G^T G), \ W = \frac{1}{\alpha}G^T, \ S = I - \frac{1}{\alpha}G^T G$$

and a proximal operator is defined as follows:

$$prox_{\lambda \phi}(X) = \pi_\lambda(a)_r = \begin{cases} \frac{\max\{0, \|X_r\|_2 - \lambda_r\}}{\|X_r\|_2} x_r & \|X_r\|_2 > 0 \\ 0 & \|X_r\|_2 = 0 \end{cases}$$

where r is a group index and the $\lambda_r$ is the corresponding thresholding parameter of the given group.

However, this iterative process requires much iteration for convergence. For relevant data (for instance, electrophysiological measurements corresponding to a given set of motions) the number of iterations can be truncated after a small number of steps used to learn the parameters defining each one of the iterations for relevant data (for instance, via stochastic gradient descent method). This method reduces the computational burden of the optimization process making it suitable for real-time applications.

Analog-to-Information Conversion

In order to recover reliably the distribution of the electrical potential on the scalp of a person usually about 100 electrodes are needed. However, the number of degrees of freedom (the number of active areas in the brain) for realistic tasks is typically much lower than the number of electrodes. It can be shown within the framework of compressed sensing theory that the number of the incoherent measurements that are needed to restore the original activation using the sparsity constraint is of the order of the degrees of freedom of this activation. Accordingly, an N-channel EEG (where N is the number of electrodes) can be multiplied by a quasirandom matrix resulting in an M-channel modified EEG where M<N, while still being able to recover the electric sources of the brain activity (the same is applicable for other electrophysiological measurements). Moreover, the quasirandom matrix can be a quasirandom matrix of ones and zeros.

Hence, instead of using N analog-to-digital converters (ADC) we can use a set of switches (much cheaper than ADCs) and just M ADCs reducing both the cost and the power consumption of the system, as is described below with reference to FIGS. 1 and 2. In addition the Appendix below provides examples of simulations illustrating the use of a reduced number of ADCs, used in a quasirandom manner, to recover the electric sources of brain activity.

Capacitive Coupling

For medical devices conductive gel is used to establish good electrical between the skin and the measuring electrode. However, for consumable electronics devices it is inconvenient to use gel. Recently, another type of electrodes, dry electrodes, have emerged that do not need conductive gel. A dry electrode exploits the effect of capacitive coupling between the electrode and the conductive parts of the body where the signal is propagating. We briefly recall here the theory of capacitive coupling between ideal conductors in dielectrics that can be adapted to account for the capacitive coupling between an electrolyte (the conductive parts of the body) and the electrodes.

Given a 3D complex structure consisting of M conductors embedded in a uniform dielectric medium characterized by permittivity $\varepsilon_b$. The capacitance matrix is defined by the relation $$Q_m = \sum_{n=1}^{M} C_{mn} V_n, m = 1, \ldots, M,$$

where $Q_m$ is the total charge on the $m^{th}$ conductor, $V_n$ is the voltage on the nth conductor, and Cmn is the capacitance between the $m^{th}$ and nth conductors. The total charge on the $m^{th}$ conductor is found by integration of the surface charge density $\sigma(x)$ over the $m^{th}$ conductor's surface $S_m$. The charge density $\sigma(x)$ is a solution of the integral equation $$\int_S \frac{1}{4\pi\varepsilon_b} \frac{1}{|x-x'|} \sigma(x')ds' = \Phi(x), x \in S,$$

where $S = \cup_{k=1}^{M} S_k$ and $\Phi(x)$ is a known impressed potential.

Here we recall that for a parallel plate capacitor the capacitance is proportional to the plate area and inversely proportional to the distance between the plates. Accordingly, for the sensing electrode the coupling capacitance decreases with the distance between the electrode and the epidermis. Consequently, once the distance from the body to the electrode is kept substantially equal for all the sensing elements the capacitance should be proportional to the number of short-circuited electrodes, when the electrodes are switched, as described above. Since the signal at the input of the acquisition channel is divided between the input capacitance of the acquisition channel and the coupling capacitance of the electrode, the deviation from the linear dependence on the number of electrodes will correspond to the distance change from the electrode to the body.

Embodiments of the present invention use this fact to reduce the motion artifact of the electrode relative to the body. Moreover, assuming a relative rigidity of the signal acquisition device (for instance, a wristband) information about the relative position of the electrode and the body (deduced from the capacitive coupling of an electrode to the body) can be used to recognize a gesture (since the contour of the wrist can be related to the gesture of the subject).

The Appendix below provides more details of the effect of the coupling capacitance of electrodes on signals acquired by the electrodes.

Figure 1:
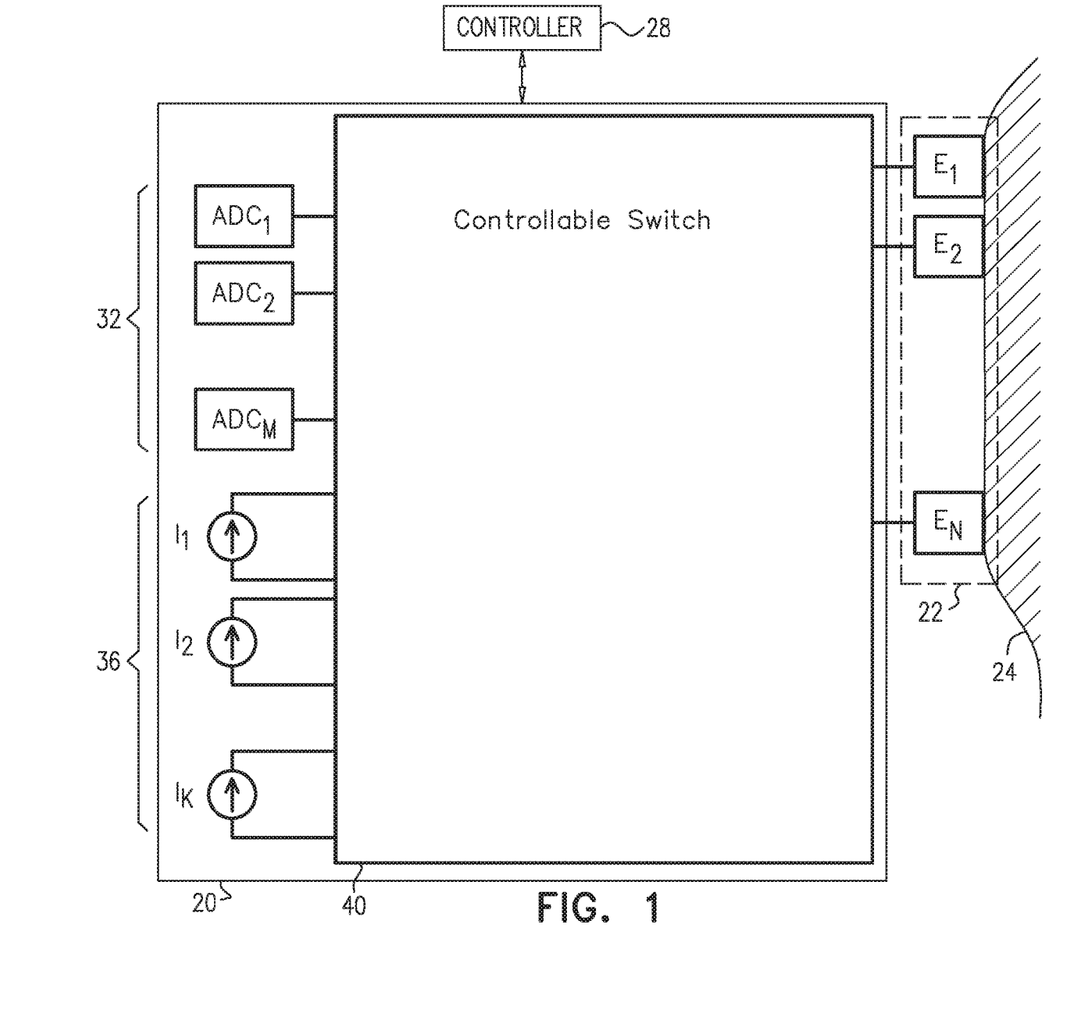
FIG. 1 is a schematic diagram of switching circuitry connected to electrodes attached to a subject, according to an embodiment of the present invention.

Reference is now made to FIG. 1, which is a schematic diagram of switching circuitry 20 connected to electrodes attached to a subject, according to an embodiment of the present invention.

Switching circuitry 20 acts as a matrix of switches, and is coupled to a first plurality of N electrodes $E_1, E_2, \ldots E_N$, also referred to herein as electrodes 22, which are in turn attached to be in proximity to an epidermis 24 of a subject. In the disclosure and in the claims, the term proximity, when referring to the attachment of the electrodes to the epidermis, is to be understood as the electrodes contacting the epidermis, and/or to be sufficiently close to the epidermis so as to be able to capacitively couple a measurable current to the epidermis. In one embodiment N=64, but there is substantially no limit on the number of electrodes that may be attached to circuitry 20. Epidermis 24 is typically a scalp or a wrist of a subject, but the epidermis may comprise another surface of the subject, such as a leg or a finger. The switching circuitry is under overall control of a controller 28, also herein termed a processor, which is typically an off-the-shelf processing unit, although in some embodiments processor 28 may at least partially comprise one or more dedicated components such as a field programmable gate array (FPGA) or an application specific integrated circuit (ASIC).

Switching circuitry 20 comprises a second plurality M of analog to digital converters ($ADC_1, \ldots ADC_M$), also referred to herein as ADCs 32, providing digitized outputs. Circuitry 20 also comprises a third plurality K of current sources ($I_1, \ldots I_K$), also referred to herein as sources 36. Circuitry 20 further comprises a controllable switch 40, which, under control of controller 28, is configured to switch between electrodes 22, ADCs 32, and current sources 36.

The current sources provide the injection currents referred to above. The current sources are illustrated as having two leads, since any particular source may inject current between any selected pair of electrodes. Controllable switch 40 switches the ADCs and the electrodes, so that the ADCs acquire and digitize signals from selected electrodes 22. Switch 40 also switches the current sources and the electrodes, so that sources 36 inject current into selected electrodes 22. The currents are typically baseband, to increase capacitive coupling. Typically each current source may have a plurality of frequencies, so increasing the amount of information that may be extracted. In an alternative embodiment the frequencies are in the range of approximately 10 kHz-approximately 1 MHz, but frequencies outside this range are also possible, such as down to 10 Hz or up to 100 GHz.

There are a number of factors associated with circuitry 20:

1) Selected electrodes 22 of interest only can be sampled reducing the number of ADCs 32 required.

2) Compressed sensing techniques can be applied by recording the combination of the measuring channels rather than each one independently. Examples of the use of these techniques are described above in the "Real time 11 norm minimization algorithm" and "Analog-to-information conversion" sections above. In one embodiment of the invention, the techniques may also be used in the flowchart of FIG. 3, as described below.

3) Capacitive coupling of the electrodes to the body can be determined by loading the electrodes with different capacitances to both update the modeling referred to above, thus improving the signal interpretation accuracy, and to discriminate between different body geometries classes (due to different gestures or different facial appearances, for instance).

4) Circuitry 20 enables application of electrical impedance tomography inducing the current through different pairs of electrodes 22 and measuring the resulting voltages on other electrodes 22, (due to the possibility to encode the currents in different frequencies there is a possibility to induce a number of currents simultaneously). This allows updating an electrical model of the body near the measured bioelectric signals so as to reveal more information from these signals (which are confined to a low frequency region).

5) Circuitry 20 enables digitally toggling the measured and induced signals (to compensate for electrode movements between the sessions and to improve the classification accuracy). An example of toggling is provided in the description of the flowchart of FIG. 3 below.

6) Circuitry 20 enables currents to be injected in parallel with signal measurements at any selected electrodes. Typically the injected current is in a narrow frequency band, so that both impedances and electrophysiological signals can be measured.

Figure 2:
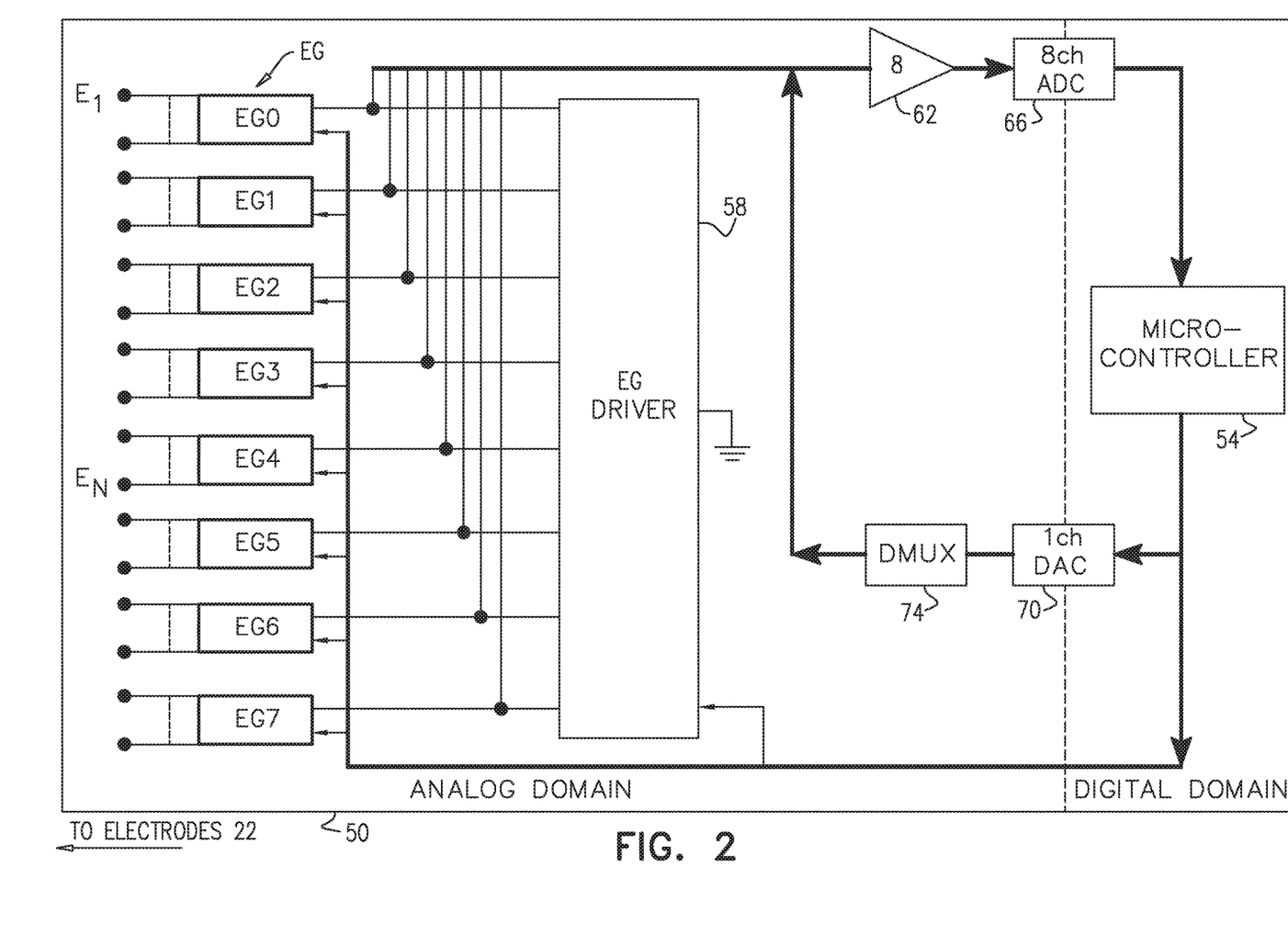
FIG. 2 is a schematic diagram of alternative switching circuitry, according to an embodiment of the present invention.

FIG. 2 is a schematic diagram of alternative switching circuitry 50, according to an embodiment of the present invention. Alternative switching circuitry 50 comprises a microcontroller 54 which acts as a processor to operate the circuitry. In one embodiment microcontroller 54 is an Arduino Due microcontroller. Circuitry 50 is connected to electrodes 22 (FIG. 1), which by way of example are assumed to comprise 128 electrodes. The connections to the electrodes are via eight electrode group connectors EG0 . . . EG7, herein also termed groups EG, which each connect to 16 electrodes 22. Groups EG are driven by an electrode group driver 58, which connects the electrodes to other elements of circuitry 50, described below.

Driver 58 and groups EG are all individually controlled by microcontroller 54, which enables the driver and the groups to access each of electrodes individually. The access enables the microcontroller to acquire signals from each of the electrodes, to inject signals into each of the electrodes, to connect electrodes together, as well as to insert impedances into lines leading to the electrodes. Thus driver 58 and groups EG act substantially as controllable switch 40 of circuitry 20 (FIG. 1).

Analog signals from electrodes 22 are fed, via groups EG, to a set of eight amplifiers 62 followed by eight respective ADCs 66, and microcontroller 54 acquires the digitized signals from the ADCs. Amplifiers 62 and ADCs 66 act substantially as ADCs 32 of circuitry 20.

Circuitry 50 also comprises a single channel digital to analog converter (DAC) 70, into which the microcontroller inputs digital signals so as to generate desired multiple analog signals. The multiple analog signals are demultiplexed in a demultiplexer (DMUX) 74, and the resultant set of analog signals may be fed, via a line 76 and groups EG, to selected electrodes 22. DAC 70 and DMUX 74 act substantially as current sources 36 of circuitry 20.

Figure 3:
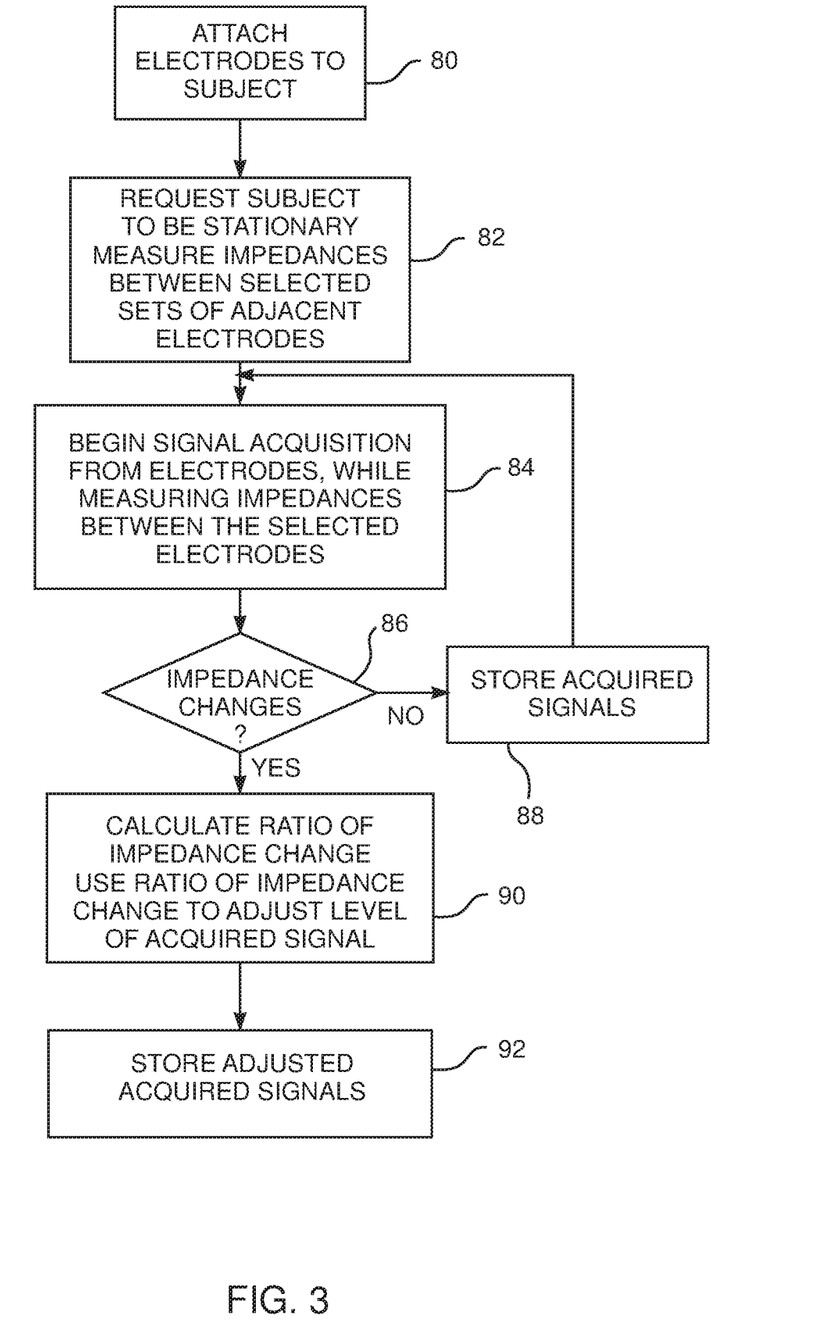
FIG. 3 is a flowchart of steps of an algorithm performed by a controller in reducing motion artifacts during acquisition of signals, according to an embodiment of the present invention.

FIG. 3 is a flowchart of steps of an algorithm performed by a controller in reducing motion artifacts during acquisition of signals, according to an embodiment of the present invention. For clarity, the steps of the flowchart are assumed to be implemented using circuitry 20 and controller 28 (FIG. 1) and those having ordinary skill in the art will be able to adapt the following description, mutatis mutandis, if circuitry 50 and microcontroller 54 are used, or if any other circuitry having the characteristics of circuitries 20 and 50 is used.

Circuitry 20 and electrodes 22 are assumed to be installed in a device worn by a subject, herein also termed a wearable device. In an embodiment controller 28 is also installed in the wearable device. In an alternative embodiment controller 28 is remote from the device, such as being operative in a smartphone of the subject, and communicates with circuitry 20 either wirelessly or via optical or electrically conductive cables.

In an attachment step 80 electrodes 22 are attached in proximity to epidermis 24. Herein, by way of example, the wearable device is assumed to be a wristband, and electrodes 22 are assumed to be affixed to the wristband, which a subject places on his/her wrist.

In a calibration step 82 of a calibration phase the subject is requested to remain stationary, and while the subject is stationary controller 28 measures impedances between pre-selected sets of electrodes in proximity to each other. The impedances are typically measured by the controller injecting known and measured currents into one of the pre-selected electrodes, and measuring the potentials generated in response at the other pre-selected electrodes using an ADC 32. Controller 28 stores the impedances evaluated in step 82 as calibration impedances $Z_{cal}$, and an indication may then be provided to the subject, for example by having a light, attached to the wristband, illuminate, that the calibration phase has completed.

In cases where the electrodes are not attached to the epidermis using gel, the impedances measured here typically have a capacitive component in an approximate range of tens of pF to 1 nF.

It will be understood that measuring impedances in this and other steps of the flowchart may comprise measuring the capacitive coupling of electrodes by shortcircuiting some of the electrodes. For example, for electrodes that are in relative close proximity to each other, and that can be assumed to have approximately equal capacitances (to the epidermis), shortcircuiting the electrodes, while measuring injected signals in the short-circuit and open-circuit stages, provides sufficient information to evaluate the capacitive coupling of each electrode.

The measured capacitances may be used in an adjustment step 90 of the flowchart, as described below.

Controller 28 then begins, in an operational step 84, an operational phase. The controller 28 may indicate to the subject, for example by extinguishing the light illuminated in calibration step 82, that the calibration phase has concluded and that the operational phase has commenced. At this point the controller begins acquiring signals from electrodes 22, in one embodiment so as to recognize a gesture of the subject. An algorithm for recognizing a gesture, using electrodes 22, is described below with reference to FIG. 4. While acquiring the signals, the controller continues to measure the impedances between the pre-selected electrodes, typically by substantially the same method as is described in step 82. Typically, while checking and reducing motion artifacts, as described in the present flowchart, as well as recognizing a gesture, as described in the flowchart of FIG. 4, controller 28 toggles between the two processes.

In some embodiments, controller 28 may apply compressed sensing techniques, as described above, in acquiring signals from electrodes 22.

In an iterative comparison step 86 the controller compares the measured impedances of the pre-selected electrodes with the impedance values stored in calibration step 82, so as to check if there are any changes in impedance. If the comparison returns negative, i.e., there are no changes to the impedances, then the flowchart continues to a signal store step 88, wherein the controller stores the signals acquired in step 84. After store step 88 control of the flowchart returns to the beginning of step 86 so as to iterate the comparison.

If comparison step returns positive, i.e., the controller detects that there are changes ΔZ in the impedance values, the flowchart continues to a signal adjustment step 90. The changes of impedance are typically due to motion of the electrodes relative to epidermis 24 of the subject.

In adjustment step 90 the controller calculates a ratio $$R = \frac{\Delta Z}{Z_{cal}}$$

and uses the value R of the ratio, as well as the values of impedances measured in step 82 and 84, to adjust the value of the signal acquired in step 84. The adjustment assumes a process of voltage division between an input impedance to ADC 32 and the capacitance of a given electrode (measured in step 84).

In a storage step 92 the controller stores the adjusted signal values, which compensate for the changes in impedance induced by the electrode motion, and control of the flowchart returns to step 84.

Figure 4:
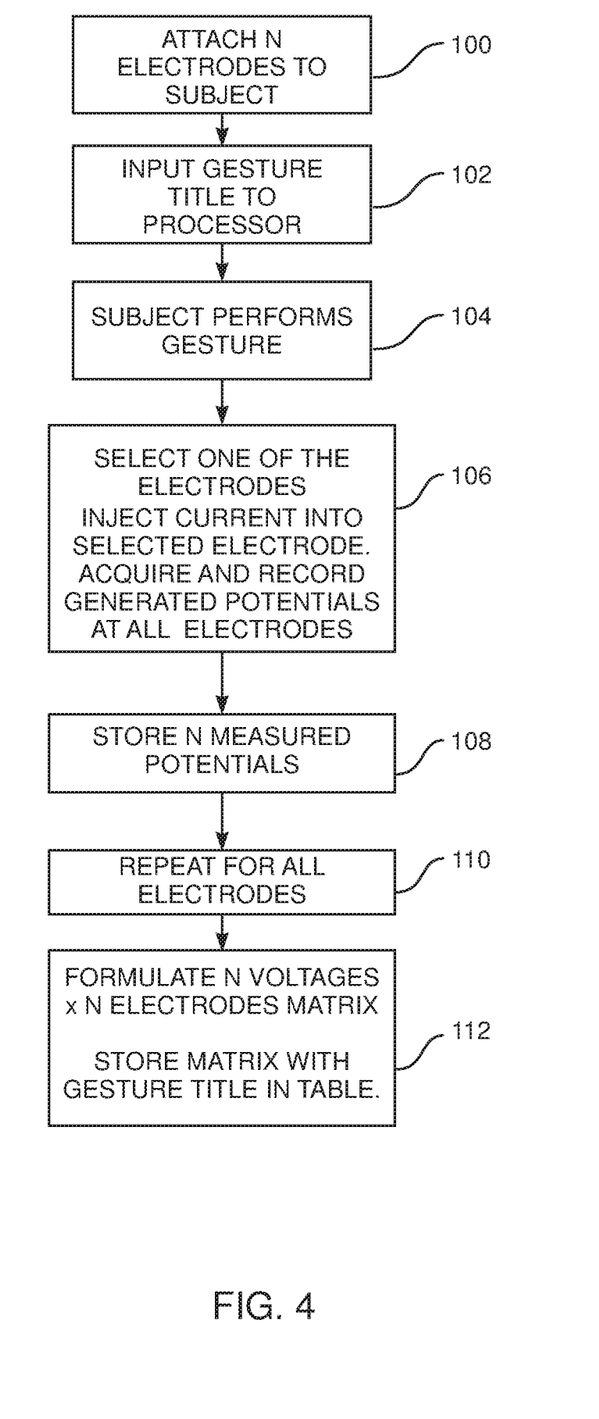
FIG. 4 is a flowchart of steps of an algorithm performed by a controller in recognizing geometry or a gesture of subject, according to an embodiment of the present invention.

FIG. 4 is a flowchart of steps of an algorithm performed by a controller in recognizing geometry or a gesture of subject, according to an embodiment of the present invention. As for the flowchart of FIG. 3, the steps of this flowchart are assumed to be implemented using circuitry 20 and controller 28 (FIG. 1).

In an attachment step 100 N electrodes 22, where N is a positive integer, are attached in proximity to epidermis 24. As for the flowchart of FIG. 3, the electrodes are assumed to be affixed to a wristband which a subject places on his/her wrist.

In a gesture indication step 102 the subject provides an indication to controller 28 of a gesture to be recognized by circuitry 20. The indication may be provided to the controller by any convenient method known in the art. For example, the subject may tap on one of a number of gestures listed in a menu presented to the subject on the subject's smartphone. The controller stores the gesture indication as an index "ges".

In a gesture performance step 104 the subject then performs the gesture, herein by way of example assumed to be the subject opening a clenched fist. While the gesture is being performed the controller 28 implements the following steps.

In an electrode selection step 106 the controller selects one of the N electrodes and injects current into the selected electrode. While the current is being injected the controller measures and acquires the potentials generated in response to the current injection on the other N−1 electrodes, as well as on the injection electrode. Typically a frequency of the current injected is approximately 40 kHz although any convenient frequency may be used. By using a specific injection frequency selected by the controller, the generated potentials on the N electrodes may be distinguished from other interfering signals. Typically, during the signal injection and potential value acquisition, the controller checks for motion artifacts and adjusts the acquired potentials as necessary, as explained above with respect to the flowchart of FIG. 3.

In a storage step 108 the controller stores the N measured potentials, adjusted to compensate for motion artifacts if necessary.

In a repetition step 110, the controller repeats the actions of steps 106 and 108.

In a final storage step 112 the controller formulates a square matrix $[M]_{ges}$ of N electrodes×N acquired potentials. The controller stores matrix $[M]_{ges}$ and gesture index ges in a gesture recognition table.

Typically the flowchart is repeated for a number of different gestures, generating respective matrices for each different gesture. Consequently, when the subject subsequently performs a gesture, the controller is able to access the gesture recognition table to recognize the gesture being performed.

While the description above has used as an example of a wearable device a wristband, it will be understood that the scope of the present invention is not limited to any particular type of wearable device, but rather includes any wearable device wherein circuitry such as circuitry 20, and electrodes such as electrodes 22, may be installed. For example, the wearable device may comprise an ankle band, a leg band, an arm band, a belt that is fixed around the waist of a subject, or a neck band.

The Appendix below provides examples of simulations performed by the inventors, using a simulation of circuitry 20. In addition, the Appendix provides details of the effect of the coupling capacitance of electrodes on signals acquired by the electrodes.

Appendix

The Simulations

Figure 5:
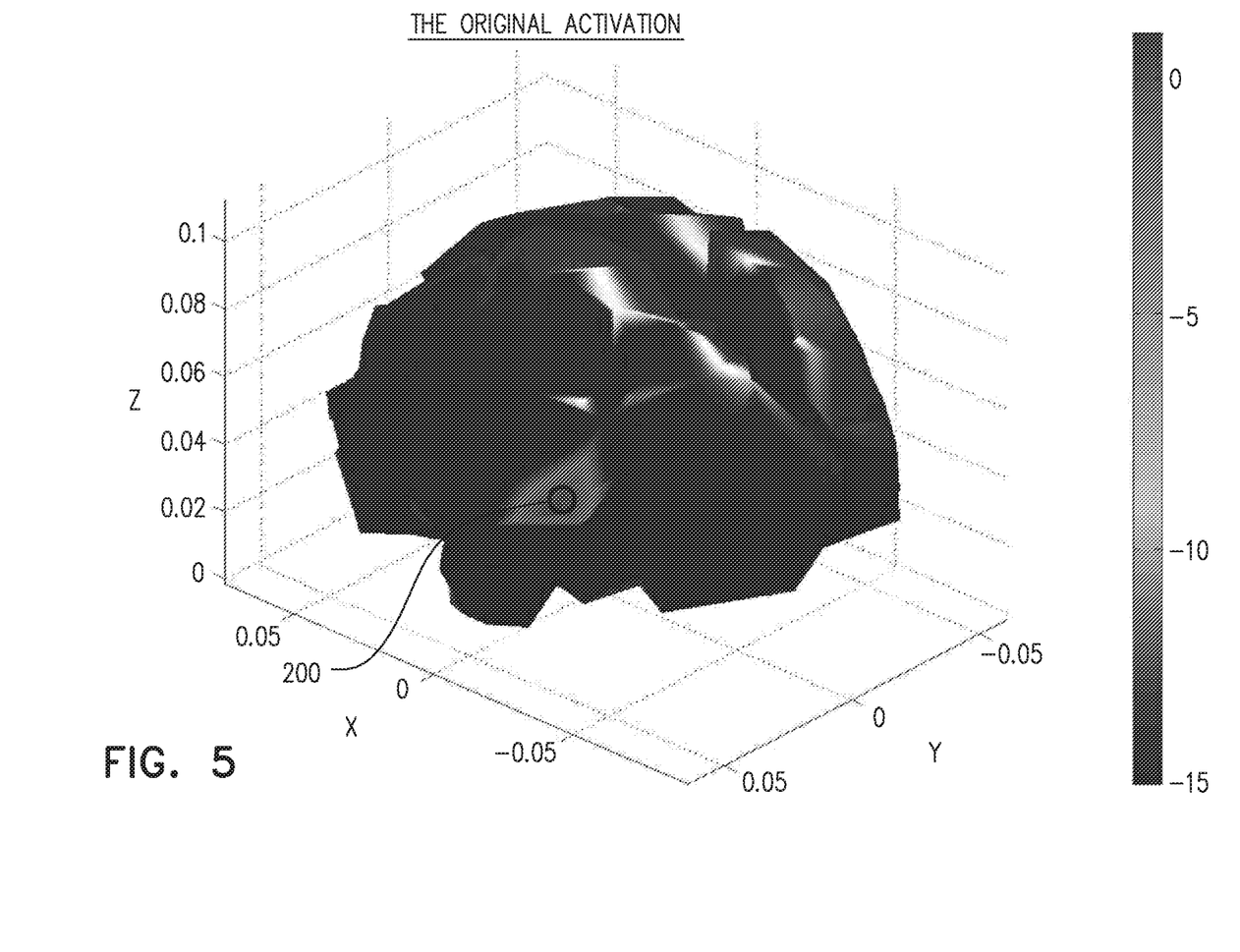
FIGS. 5-8 show activations of the brain, according to an embodiment of the present invention.

FIGS. 5-8 show activations of the brain, according to an embodiment of the present invention. FIG. 5 shows an original activation of the brain in a region 200. In this case we took a model of a brain comprising 300 sources and 64 electrodes in a standard 10-20 configuration. In what follows we show that using a random modulator the number of sensing electrodes can be reduced to 8.

Figure 6:
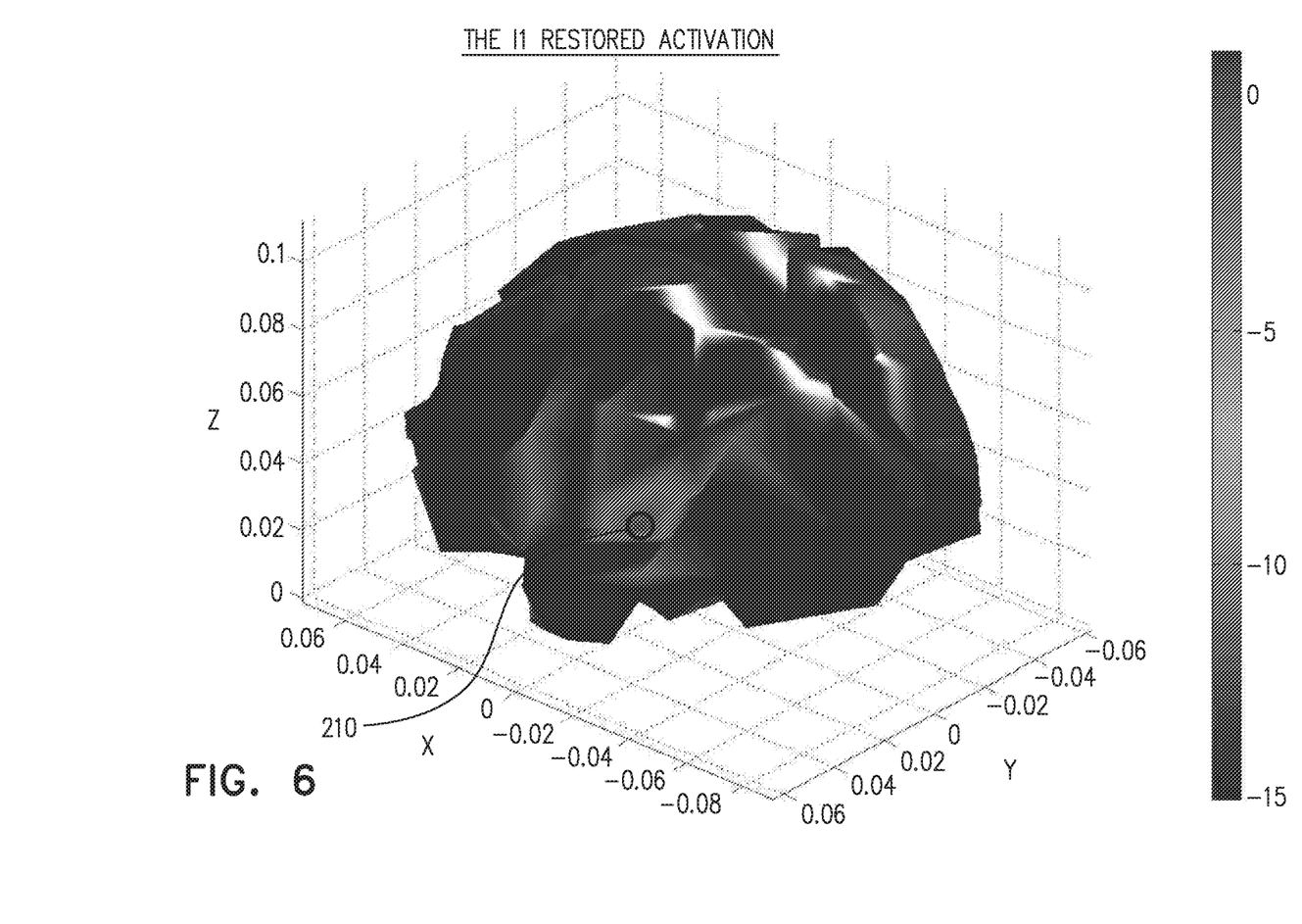

FIG. 6 illustrates that, as expected, the original activation, at a region 210, is easily recovered from the EEG using an $l_1$ norm.

Figure 7:
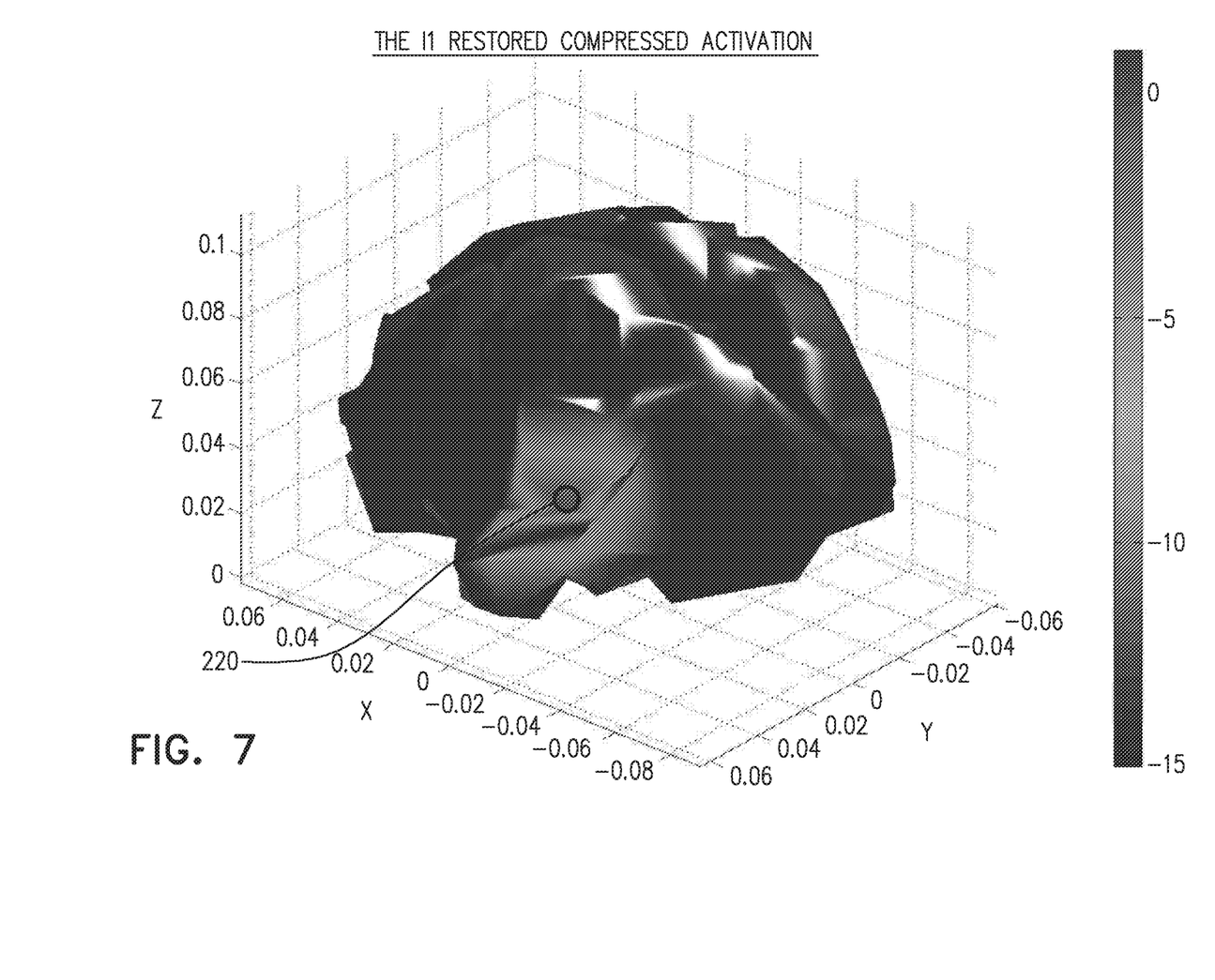

For FIG. 7 we multiply the 64 electrode EEG signal by a quasirandom 64×8 matrix of ones and zeros. FIG. 7 illustrates that the activation is still resolved at a region 220.

Figure 8:
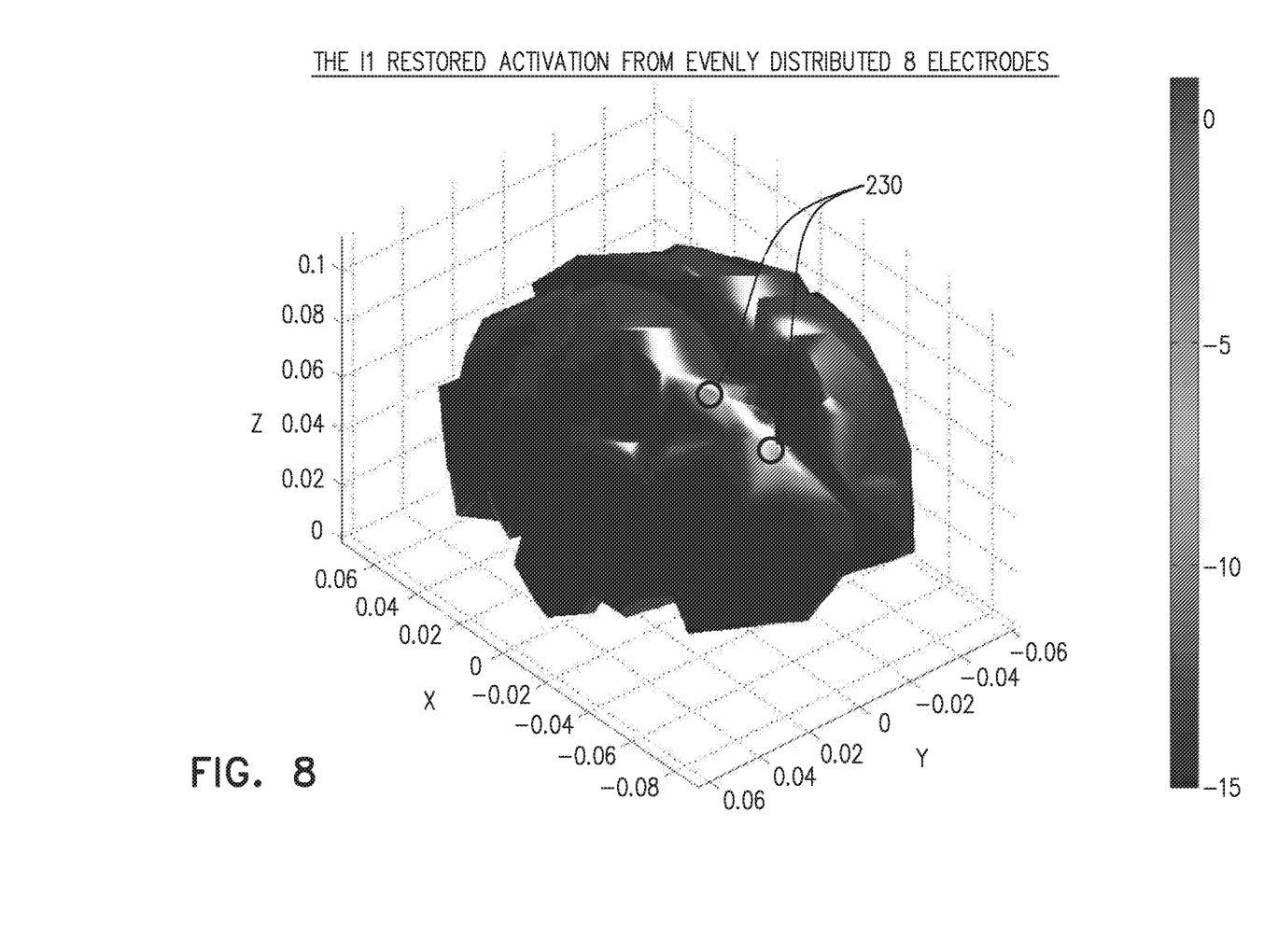

However, if we take 8 evenly distributed electrodes on the scalp and try to resolve the same activation, we can see in FIG. 8 that it was not recognized correctly (instead of one focused activation at substantially identical regions 200, 210, and 220 two focused activations emerged at different regions 230).

We conclude that random modulation of the signal permits reducing the number of electrodes without altering the solution quality. However, simply reducing the number of electrodes results in erroneous solutions.

Coupling Capacitance

Figure 9:
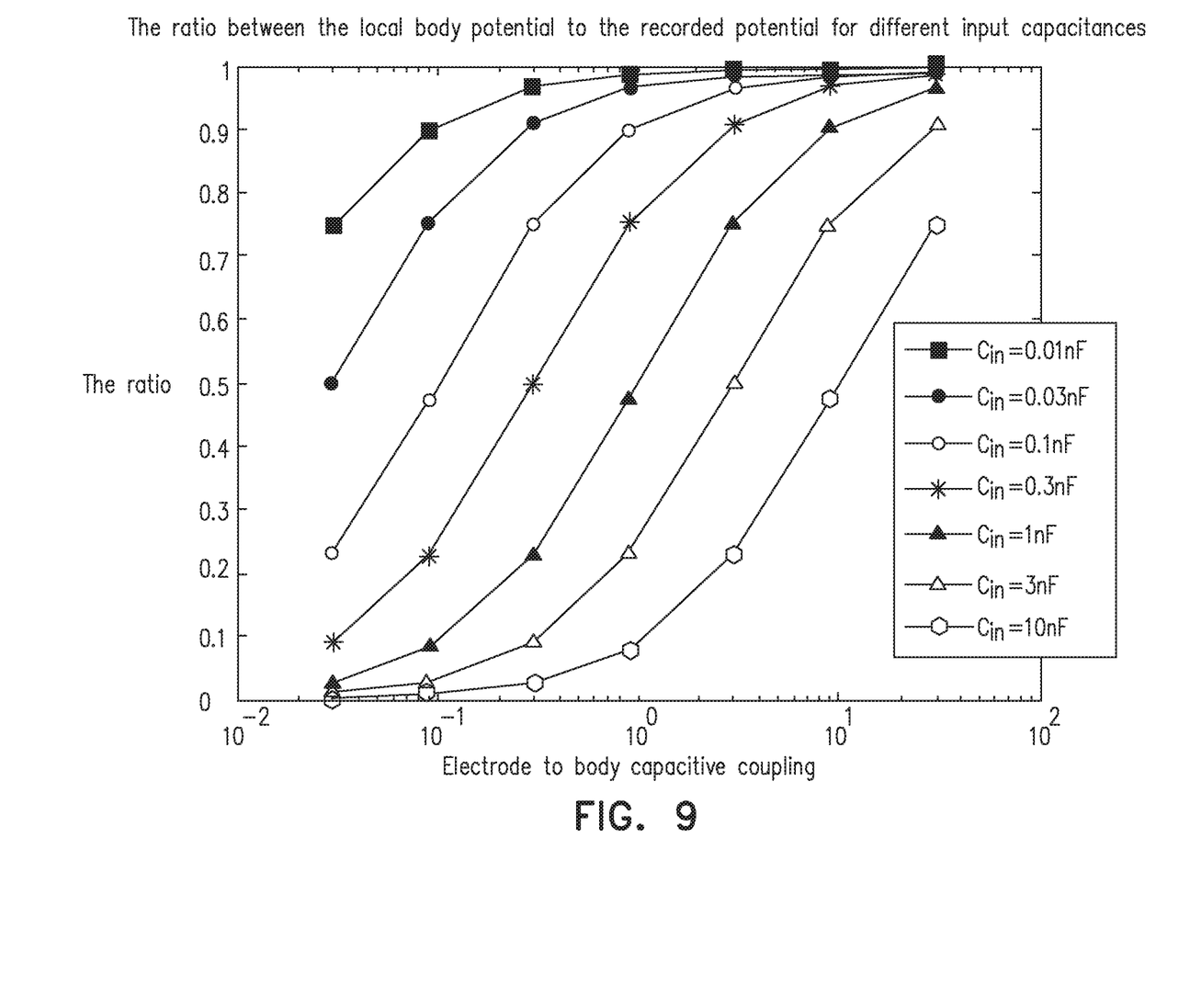
FIG. 9 plots the ratio of the local body potential to the recorded potential vs. the electrode to body capacitive coupling, according to an embodiment of the present invention.

FIG. 9 plots the ratio of the local body potential to the recorded potential vs. the electrode to body capacitive coupling, according to an embodiment of the present invention. The ratio is plotted for different input capacitances.

Here we explore the influence of the coupling capacitance for different numbers of electrodes and different input capacitance of the acquisition channel on the signal amplitude assuming a unit source. We assumed values of the input capacitances of the acquisition channel are in the range 10 pF-10 nF, and the range of the coupling capacitances of the electrode to the body is 30 pF-30 nF.

The figure shows that for a given input capacitance the input signal varies substantially when the capacitive coupling is altered. Hence by changing the number of electrodes switched to the given acquisition channel (and hence the capacitive coupling) the signal at the input is altered sufficiently to decode the relative position of the electrode and the body.

It will be appreciated that the embodiments described above are cited by way of example, and that the present invention is not limited to what has been particularly shown and described hereinabove. Rather, the scope of the present invention includes both combinations and subcombinations of the various features described hereinabove, as well as variations and modifications thereof which would occur to persons skilled in the art upon reading the foregoing description and which are not disclosed in the prior art.

The invention claimed is:

1. Apparatus, comprising:
a set of N electrodes, configured to be located in proximity to an epidermis of a subject, and to acquire N respective input signals generated by electric sources within the subject;
a set of M channels, where M is less than N;
a switch, configured to multiply the N input signals by a quasirandom N X M matrix of ones and zeros to generate M output signals from the N electrodes, including short-circuiting selected ones of the N electrodes, and to direct the M output signals to the M channels; and
a processor, configured to control the switch, and to receive and analyze the M output signals obtained from the M channels while modulating the quasirandom N×M matrix to compute, based on the output signals, respective timecourses of the electric sources within the subject.

2. The apparatus according to claim 1, wherein the processor is configured to determine respective amplitudes of the electric sources.

3. The apparatus according to claim 1, and comprising respective current sources, and wherein the processor is configured to activate the switch so as to inject respective predetermined currents from the current sources between selected pairs of the N electrodes.

4. The apparatus according to claim 3, wherein the injected currents have a plurality of baseband frequencies.

5. The apparatus according to claim 3, wherein the injected currents have frequencies between 10 Hz and 100 GHz.

6. The apparatus according to claim 1, wherein the switch comprises a matrix of switches.

7. The apparatus according to claim 1, wherein at least one of the electrodes is capacitively coupled to the epidermis.

8. The apparatus according to claim 1, wherein the signals comprise sparse activations.

9. The apparatus according to claim 1, wherein the N electrodes, the M channels, the switch, and the processor are comprised in a wearable device.

10. The apparatus according to claim 9, wherein the wearable device comprises one of an ankle band, a leg band, an arm band, a belt that is fixed around a waist of the subject, and a neck band.

11. The apparatus according to claim 1, wherein the N electrodes, the M channels, and the switch are comprised in a wearable device, and wherein the processor is remote from the wearable device.

12. The apparatus according to claim 11, wherein the wearable device comprises one of an ankle band, a leg band, an arm band, a belt that is fixed around a waist of the subject, and a neck band.

13. The apparatus according to claim 1, wherein the processor is configured to determine respective positions of the electric sources.

14. The apparatus according to claim 1, wherein the processor is configured to process the output signals obtained from the M channels while modulating the quasirandom N×M matrix to identify a set of the output signals having a minimum noise and to apply the identified set in computing the respective timecourses of the electric sources.

15. A method, comprising:
locating a set of N electrodes in proximity to an epidermis of a subject so as to acquire N respective input signals generated by electric sources with the subject; providing a set of M channels, where M is less than N;
multiplying the N input signals by a quasirandom N×M matrix of ones and zeros, using a switch, to generate M output signals from the N electrodes, including short-circuiting selected ones of the N electrodes, and directing the M output signals to the M channels; and
a processor configured for receiving and analyzing the M output signals obtained from the M channels while controlling the switch the modulate the quasirandom N×M matrix to compute, based on the output signals, respective timecourses of the electric sources within the subject.

16. The method according to claim 15, and comprising determining respective amplitudes of the electric sources.

17. The method according to claim 15, and comprising providing respective current sources, and activating the switch so as to inject respective predetermined currents from the sources between selected pairs of the N electrodes.

18. The method according to claim 17, wherein the injected currents have a plurality of baseband frequencies.

19. The method according to claim 17, wherein the injected currents have frequencies between 10 Hz and 100 GHz.

20. The method according to claim 15, wherein the switch comprises a matrix of switches.

21. The method according to claim 15, wherein at least one of the electrodes is capacitively coupled to the epidermis.

22. The method according to claim 15, wherein the signals comprise sparse activations.

23. The method according to claim 15, further comprising:
selecting a subset of the N electrodes that are in proximity with each other;
measuring impedances of the subset relative to each other; and
when the impedances change, using the change of impedances to estimate a change in the acquired signals, and applying the change in the acquired signals so as to correct the acquired signals.

* * * * *